United States Patent [19]

Bailon et al.

[11] Patent Number: 5,162,503
[45] Date of Patent: Nov. 10, 1992

[54] PURIFICATION OF INTERLEUKIN-2 BY RECEPTOR-AFFINITY CHROMATOGRAPHY

[75] Inventors: Pascal Bailon, Florham Park, N.J.; John E. Smart, Weston, Mass.; David V. Weber, Nutley, N.J.

[73] Assignee: Hoffmann-La Roche, Inc., Nutley, N.J.

[21] Appl. No.: 51,967

[22] Filed: May 19, 1987

[51] Int. Cl.⁵ .................. C07K 15/00; C07K 3/20; C07K 17/00; G01N 33/50
[52] U.S. Cl. .................. 530/388.2; 530/389.2; 530/391.1; 530/391.5; 530/388.23; 530/351; 530/402; 530/403; 530/404; 530/405; 530/406; 530/409; 530/410; 530/411; 530/412; 530/413; 530/810; 530/811; 530/812; 530/813; 530/814; 530/417; 530/422; 435/7.1; 435/7.8; 435/69.1; 436/501; 436/518; 436/524; 436/527; 436/528; 436/529; 436/530; 536/56; 536/112
[58] Field of Search .......... 530/351, 409–412, 530/413, 417, 350, 422, 825, 810–814, 387, 389–391, 402–406, 409–410; 435/68, 69.1, 71, 7.8; 436/518, 524, 527–530, 824

[56] References Cited

U.S. PATENT DOCUMENTS

4,560,649 12/1985 Saxena et al. .................. 435/7
4,578,335 3/1986 Urdal et al. .................. 530/351

FOREIGN PATENT DOCUMENTS

0091539 10/1983 European Pat. Off.
0145390 6/1985 European Pat. Off.
210645 7/1986 European Pat. Off.

OTHER PUBLICATIONS

Treiger* et al., J. Immunol. 136:4099–4105 (1986).
Bailon et al., Biotechnology 5:1195–98 (1987).
K. L. Bost et al., Proc. Natl. Acad. Sci. U.S.A., 82:1372–75 (1985).
Rasmussen and Hesch, Biochem. Biophys. Res. Commun. 149:930–38 (1987).
Parokh et al. C and EN, Aug. 1985 pp. 17–32.
Sharon et al, Science 234, 1986, pp. 859–863.
Linthicam et al BioEssay 3(5) 1985, pp. 213–217.
Stadler et al, J. Immunology 128, 1982, pp. 1620–1624.
Smith et al J. Immunology 131, 1983, pp. 1808–1815.
Robb et al J. Exp Med 1984, 1160, pp. 1126–1146.
Cosman et al., Nature 312:768 (1984).
Jarrett et al., Australian Patent Application No. AU-A-17965/83.
Leonard et al., Nature 311:625 (1984).
Miller et al., J. Immunol. 134:4212 (1985)
Nikaido et al., Nature 311:631 (1984).
Shimuzu et al., Nucleic Acids Res. 13:1505 (1985).
Treiger et al., J. Immunol. 136:4099 (1986).

Primary Examiner—Garnette D. Draper
Attorney, Agent, or Firm—George M. Gould; William H. Epstein; Patricia S. Rocha

[57] ABSTRACT

Methods are provided for the purification of interleukin-2 (IL-2) from a wide variety of sources, including synthetic mixtures, culture medium conditioned by natural IL-2 producing cells, and mammalian and bacterial recombinant IL-2 expression systems. The methods of the invention employ IL-2 receptor-affinity adsorbents in which soluble IL-2 receptors have been immobilized on solid supports. Through the use of these affinity adsorbents, highly purified IL-2 can be produced in a single step from bacterial extracts or conditioned medium. The IL-2 thus purified is largely free of aggregated forms, which are often present when other purification methods are used.

14 Claims, 5 Drawing Sheets

PURIFICATION OF INTERLEUKIN-2 BY RECEPTOR-AFFINITY CHROMATOGRAPHY

TABLE OF CONTENTS

1. Technical Field
2. Background of the Invention
    2.1. Purification of Biologically Active Proteins and Polypeptides
    2.2. Cloning and Expression of IL-2 Receptors
3. Summary of the Invention
4. Brief Description of the Figures
5. Detailed Description of the Invention
    5.1. Sources of IL-2
    5.2. IL-2 Receptors
    5.3. Support Materials
    5.4. Coupling Agents
    5.5. Applications of IL-2 Receptor-Affinity Adsorbents
    5.6. IL-2 Desorption
6. Examples
    6.1. General Methods
    6.2. Preparation of Interleukin-2
    6.3. Production and Purification of Recombinant Soluble IL-2 Receptors
    6.4. Immobilization of IL-2 Receptors
    6.5. Purification of Recombinant IL-2 From *E. coli*
    6.6. Purification of Recombinant IL-2 From Mammalian Cells
    6.7. Analysis of the Purified IL-2s
    6.8. Receptor-Affinity Purification of IL-2 Analogs

1. TECHNICAL FIELD

This invention relates to methods for the purification of interleukin-2. Soluble receptors for interleukin-2 produced through the use of recombinant DNA technology are immobilized on a solid support and used to prepare biologically active, unaggregated and highly purified interleukin-2.

2. BACKGROUND OF THE INVENTION 2.1. Purification of Biologically Active Proteins and Polypeptides In recent years, a wide variety of important biologically active molecules has been isolated from natural sources or produced by recombinant DNA technology. Many of these molecules are polypeptides or proteins which exert their biological effects by binding to specific cellular receptors.

To purify these polypeptides and proteins, conventional methods such as preparative electrophoresis, gel filtration chromatography, salt or organic solvent fractionation, ion exchange chromatography and the like have often been employed. The problem with the use of such conventional methods is that they are not generally specific for the protein of interest. As a consequence, many of these methods must generally be used in combination before a substantially pure protein can be obtained. Because there are losses due to analytical sampling and incomplete recovery at each purification step, the overall yields are often poor in such multistep purification procedures.

More recently, improved results have been obtained by using immunoaffinity columns containing polyclonal or monoclonal antibodies specific for a protein that is to be purified. For example, Kung, U.S. Pat. No. 4,476,049, has used immobilized monoclonal antibodies specific for the carboxyl terminus of recombinant human immune interferon to purify that protein. The use of immunoaffinity columns can lead to highly purified or even homogeneous protein preparations, but proteins purified in this way may not have their full intrinsic bioactivity.

Pestka, U.S. Pat. No. 4,623,621, has disclosed that many important biologically active polypeptides and proteins can aggregate, forming dimers, trimers and higher oligomeric forms. When such aggregation occurs, the polypeptide or protein may have either lower biological activity or no activity at all. Furthermore, such aggregated material may have the potential for causing deleterious side effects such as antibody production in patients, if it is used therapeutically. Immunoaffinity columns do not necessarily discriminate between the aggregated and unaggregated (monomeric) forms of polypeptides and proteins.

The probability that aggregation of desired polypeptides and proteins will occur is substantially increased when they are produced by recombinant DNA techniques in host organisms and isolated from cell lysates, under conditions and in concentrations that do not occur when they are produced under natural conditions. These conditions can favor aggregation through intermolecular disulfide bridges, other covalent bonds or non-covalent interactions.

2.2. Cloning and Expression of IL-2 receptors

Because most if not all biologically active polypeptides and proteins act b binding to specific cellular receptors, there have been numerous efforts in recent years to characterize these receptors. Recently, the methods of recombinant DNA technology have been brought to bear on the problem of producing receptor molecules for study. Significant progress in this area has been made in the cloning and expression of genes coding for receptors for interleukin-2.

Interleukin-2 (IL-2) is a hormone-like protein growth factor secreted by certain T lymphocytes after antigenic or mitogenic stimulation. The actions of IL-2 are mediated through the binding of the IL-2 protein to specific high affinity receptors which are present in the membranes of activated, but not resting, lymphocytes.

Miller et al. [J. Immunol. 134:4212 (1985)] and Shimuzu et al. [Nucleic Acids Res. 13:1505 (1985)] have cloned and expressed cDNA prepared from murine mRNA coding for the mouse IL-2 receptor. Leonard et al. [Nature 311:625 (1984)] and Nikaido et al. [Nature 311:631 (1984)] have described similar studies based on the human IL-2 receptor. In all of these studies, plasmids bearing IL-2 receptor-encoding inserts were used to transfect COS cells. The transfected cells were then found by specific antibody or IL-2 binding to have the expressed IL-2 receptors in their cell membranes. There was no indication in these studies that receptor molecules had been secreted into the culture medium.

More recently, Treiger et al. [J. Immunol. 136:4099 (1986)] have disclosed the expression of a secreted form of the human IL-2 receptor. This secreted form of the receptor was produced by cleaving a plasmid containing a full length IL-2 receptor cDNA with the Nae I restriction endonuclease, to delete nucleic acid sequences coding for the intracytoplasmic segment and most of the putative transmembrane segment of the complete receptor molecule. The resulting modified cDNA was then transfected into and expressed in modified mouse L cells. The polypeptide thereby produced was secreted into the medium, because its "anchor" components had been deleted.

3. SUMMARY OF THE INVENTION

This invention provides IL-2 receptor-affinity adsorbents comprising soluble IL-2 receptor molecules immobilized on a solid support, and methods for the purification of IL-2 which employ such adsorbents. These methods are applicable to the purification of IL-2 from any source, whether the IL-2 is chemically synthesized or obtained from natural sources or from recombinant DNA expression systems.

In one embodiment of the invention, IL-2 in a solution or in a culture medium conditioned by human or animal cells producing IL-2 is purified by a method comprising:

(a) contacting a solution or conditioned medium containing IL-2 with a receptor-affinity absorbent comprising soluble IL-2 receptor molecules immobilized on an insoluble support, which immobilized receptor molecules are capable of specifically binding to the IL-2;

(b) allowing the IL-2 to specifically bind to the adsorbent;

(c) washing the adsorbent to remove unbound contaminating substances;

(d) desorbing the IL-2 from the washed adsorbent; and (e) separating the receptor-affinity adsorbent from the desorbed IL-2.

In another embodiment of the invention, recombinant IL-2 produced in a bacterial expression system is purified by a method comprising:

(a) disrupting cultured bacterial cells transformed by a vector capable of directing the expression of IL-2, to produce a cell lysate;

(b) isolating the insoluble fraction from the cell lysate;

(c) extracting the isolated insoluble fraction from the cell lysate with a solution of from about 4 to 7M guanidine-HCl to obtain an IL-2 containing extract;

(d) diluting the IL-2 containing extract from about 10- to about 1,000-fold with a guanidine-HCl free solution;

(e) contacting the diluted IL-2 containing extract with a receptor-affinity adsorbent comprising soluble IL-2 receptor molecules immobilized on an insoluble support, which immobilized receptor molecules are capable of specifically binding to the IL-2;

(f) allowing the IL-2 to specifically bind to the adsorbent;

(g) washing the adsorbent to remove unbound contaminating substances;

(h) desorbing the IL-2 from the washed adsorbent; and (i) separating the receptor-affinity adsorbent from the desorbed IL-2.

Although the degree of dilution in step (d) may range from about 10- to about 1,000-fold, a dilution of the extract of about 30- to about 50-fold is preferred.

In still another embodiment of the invention, recombinant IL-2 produced in a bacterial expression system is purified as described above, except that extraction step (c) is preceded by preextraction steps to extract contaminating cellular materials, comprising extracting the isolated insoluble fraction from the cell lysate with (i) a buffered salt solution; and (ii) a solution of from about 1.75 to 2M guanidine-HCl.

In still another embodiment of the invention, recombinant IL-2 produced in a bacterial expression system is purified as described above, except that dilution step (d) is followed by a step comprising allowing the diluted extract to stand for a period of time ranging from about four hours to more than three days. Preferably the diluted extract is allowed to stand for about 1 to about 3 days.

4. BRIEF DESCRIPTION OF THE FIGURES

This invention may be more readily understood by reference to the detailed description below and to the following figures, in which.

5. DETAILED DESCRIPTION OF THE INVENTION

Figure 1:
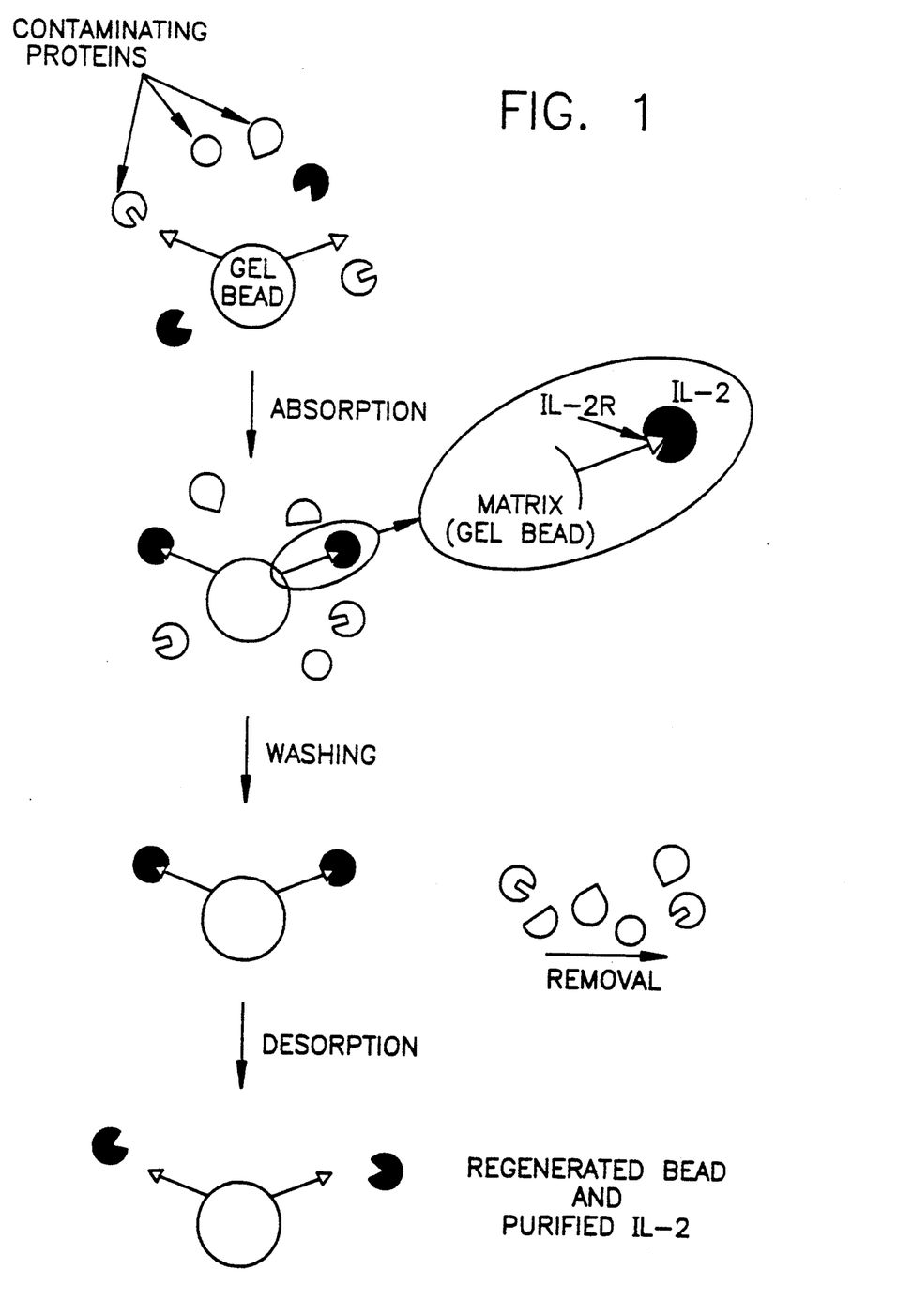
FIG. 1 is a schematic illustration of the principle of IL-2 receptor-affinity chromatography.

The present invention achieves superior purification of IL-2 through the use of receptor-affinity chromatography, a process that is schematically illustrated in FIG. 1. In this process, a bacterial extract or a solution or conditioned medium containing IL-2 is contacted with an insoluble support, to which purified, soluble receptors for IL-2 (IL-2R) have been immobilized. In FIG. 1, IL-2R molecules, represented as arrows, have been affixed to gel beads.

Because only IL-2 in the extract, solution or medium has specific high affinity for the immobilized receptors, only IL-2 will bind (or be adsorbed) to the beads. As a consequence, all of the contaminating proteins which lack such high affinity remain unbound and are readily washed away. The IL-2 specifically bound to the beads can then be desorbed by an appropriate means to produce regenerated beads and purified IL-2.

5.1. SOURCES OF IL-2

IL-2 that can be purified by the methods of this invention can be obtained from many sources. For example, it could be chemically synthesized, using published sequence data and wet or solid-state methods. Taniguchi et al., supra, have disclosed the amino acid sequence of human IL-2. The amino acid sequence of murine IL-2 has been published by Yokota et al., Proc. Natl. Acad. Sci. USA 82:68 (1985). IL-2 can also be produced by recombinant DNA methodology based upon known gene sequence data, vectors and methods, in bacterial or mammalian cell expression systems.

Transformed bacteria producing recombinant IL-2 must generally be disrupted using methods known in the art such as sonication. French pressure cell disruption or other mechanical means, osmotic shock or repeated freezing and thawing.

Cultures of lymphocytes or T cell lines can also serve as sources of IL-2. For example, Gillis et al., J. Exp. Med. 152:1709 (1980) have described the production of IL-2 in medium conditioned by cultured mouse, rat or human lymphocytes, or leukemic murine or human T cell lines. Such cultured cells are generally stimulated to produce IL-2 by agents such as phytohemagglutinin or concanavalin A. The receptor-affinity adsorbents of this invention are especially useful for such conditioned media because of their ability to selectively remove IL-2 from large volumes of medium.

5.2. IL-2 RECEPTORS

The IL-2 receptors of the invention can be any receptors specific for IL-2 that are soluble. In the preferred embodiment, an "anchor minus" modification of the human IL-2 receptor described by Treiger et al., supra, is used. This molecular is soluble because the carboxy terminal 28 amino acid residues have been deleted, thereby preventing retention of the molecule in the membranes of producing cells. Because the entire human IL-2R gene has been cloned and sequences [Cosman et al., Nature (London) 312:768 (1984)], variants containing more or fewer amino acid residues which have the requisite characteristics can readily be produced by organic synthetic or recombinant means known in the art.

Because sequence data are also available for the IL-2 receptors of the mice [Miller et al., J. Immunol. 134:4212 (1985)], soluble forms of those receptors can also be prepared by analogy to the human receptors.

There is 61% homology between the amino acid sequences of murine and human IL-2R [Miller et al., J. Immunol. 134:4212 (1985)], suggesting that there may be cross reactivity between IL-2s from these species and their IL-2 receptors. In fact, murine recombinant IL-2 binds to human IL-2R receptor-affinity adsorbent and can thus be purified using such adsorbent.

Any receptors used in this invention should preferably have the following characteristics:
1. They should be soluble to facilitate purification, preferably to homogeneity;
2. The genes encoding them should be amenable to cloning and high level expression, so that appreciable quantities can be obtained; and
3. Once immobilized to an appropriate solid support, they should still recognize and bind to IL-2 with high affinity.

5.3. SUPPORT MATERIALS

Solid supports that can be used include but are not limited to agarose gels; cross-linked agarose gels; controlled-pore glass beads, preferably coated with glycerol- and glycol-like structures to eliminate nonspecific protein adsorption; cellulose particles; polyacrylamide gel beads and cross-linked dextrans such as Sephadex ®. A modified polyhydroxy silica support is preferred, as described below.

The soluble IL-2 receptors of the invention can be directly coupled to a solid support or can alternatively be separated from the support by one of the numerous linker molecules that are known in the art. For some examples of such linker molecules that can be used, see, e.g., Lowe et al., Int. J. Biochem. 13:33 (1981).

5.4. COUPLING AGENTS

Selection of an agent for covalently coupling IL-2 receptors to the insoluble support is dependent upon the nature of the support used. For carbohydrates such as agarose or cellulose, reaction with cyanogen bromide in aqueous alkali can be used to produce an activated support, to which proteins or polypeptides will immediately couple. Already prepared cyanogen bromide activated agarose is available commercially. Bisoxiranes and epihalohydrins can also be used for this purpose [Porath et al. J. Chromatogr. 60:167 (1971); Nishikawa et al., J. Solid-Phase Biochem. 1:33 (1976)].

Derivatized polyacrylamide gels can be prepared by treatment with hydrazine, after which a variety of acylating and alkylating reagents can be used for further chemical conversion [Inman et al., Biochemistry 8:4074 (1969).

Controlled-pore glass can be treated with γ-aminopropyltriethoxysilane to cover silanol groups that give rise to nonspecific adsorption by proteins. The γ-aminopropyl moiety provides attachment points to which IL-2 receptors may be coupled. Derivatives of the glycerol- or glyco-phase coated glass beads can be obtained by treatment with sodium periodate [Sanderson et al., Immunochem. 8:163 (1971)].

For general reviews on coupling reactions, see Weliky et al., Immunmochem. 2:293 (1965) and Guilford, Chem. Soc. Rev. 2:249 (1973).

5.5. APPLICATIONS OF IL-2 RECEPTOR-AFFINITY ADSORBENTS

The IL-2 receptor-affinity adsorbents of this invention can be used in column chromatographic procedures as described below or in batch processes. Batch processes are preferable where the adsorbent produces poor flow rates or clogs in column operation, or when long contact times are needed to ensure complete IL-2 binding.

In batch operation, the immobilized IL-2R is simply suspended with stirring or agitation in the IL-2 containing extract, solution or conditioned medium for a desired amount of time, after which the adsorbent is separated by filtration or sedimentation, or by decantation or aspiration of the fluid phase after the adsorbent has been allowed to settle. The adsorbent can then be washed and the bound IL-2 can be desorbed.

A variation of the batch method called "tea-bag" batch can also be used. In this method, the IL-2 receptor-affinity adsorbent is contained within a porous bag made of fabric or other material. The bag is then immersed in the IL-2 containing extract, solution or conditioned medium for an appropriate time, after which it is removed like a tea bag. The advantage of the method is that it provides for easy separation of the adsorbent and simplified processing.

5.6. IL-2 DESORPTION

Once IL-2 has been bound to the IL-2 receptor-affinity adsorbent and the adsorbent has been washed to remove contaminating materials, the IL-2 must be released. In a preferred embodiment, a low pH desorbing solution containing 0.2N acetic acid and 0.2M NaCl is used. In general, changes in pH, ionic strength or solvent composition (such as by adding water-miscible organic solvents or chaotropic agents) can be used. Such changes must diminish the strength of the interaction between the IL-2 and the immobilized IL-2R to the point where the bound IL-2 is released (desorbed). Care must be taken, however, to ensure that the desorption conditions are not so severe as to irreversibly denature the IL-2. It is also desirable that the desorption conditions not irreversibly denature the IL-2R, so that the adsorbent can be used repeatedly.

6. EXAMPLES

6.1. GENERAL METHODS

Unless otherwise noted, protein determinations were carried out by the method of Lowry et al., *J. Biol. Chem.* 193:265 (1951), using bovine serum albumin as a standard. Values thereby obtained were confirmed by quantitative amino acid analysis. Amino acid analysis was performed as described by Pan et al., Methods of Protein Microcharacterization (Shively, J. E., Ed.), The Humana Press Inc., Clifton, N.J., p. 105 (1986), following hydrolysis of the samples in 6N HCl containing 4% thioglycolic acid at 110° C. for 20-24 hours in vacuo. Proline and cysteine values were determined after performic acid oxidation. Sodium dodecyl sulfate (SDS) polyacrylamide gel electrophoresis was performed in 12% gels as described by Laemmli, *Nature* (London) 227:680 (1970).

IL-2 bioassays were carried out using a colorimetric modification of the method of Gillis et al., *J. Immunol.* 120:2027 (1978). In this assay CTLL cells, cells of a murine cytotoxic lymphoid cell line dependent upon IL-2 for growth [Gillis et al., *J. Exp. Med.* 164:468 (1977)], were used as target cells. CTLL cells (Immunex Corp., Seattle, Wash.) were maintained in RPMI-1640 medium (Gibco Laboratories, Grand Island, N.Y.) supplemented with 5% (v/v) fetal calf serum (Gibco), 25 mM HEPES buffer, 50 µg/ml gentamicin (Schering-Plough Inc., Bloomfield, N.J.) and 200 units/ml crude human IL-2.

For assay, CTLL Cells were removed from the IL-2 containing maintenance medium by sedimentation for 10 minutes at 500×g in a Beckman Model J-6B centrifuge, and washed twice in HB101 medium (Hana Biologicals, Berkeley, Calif.) without IL-2. The cells were resuspended to a concentration of $2 \times 10^5$ cells/ml in HB101 supplemented with 50 µg/ml gentamicin. Samples to be titrated were diluted in HB101 in the first wells of a row in a half-area microtiter plate (Costar No. 3696) to a final volume of 0.1 ml. Subsequent wells in the rows contained 0.05 ml of HB101, and twofold dilutions of the samples were made by transferring 0.05 ml aliquots serially to the end of the rows. Several wells filled with 0.05 ml of medium without IL-2 served as negative controls. All wells were seeded with 0.05 ml of the cell suspension, and the plate was covered with a plastic lid and incubated for 20 hours at 37° C. in a humidified, 5% $CO_2$ chamber.

This assay is based upon a colorimetric determination of lactic acid (LA) produced as an end product of glucose metabolism by stimulated cells. Reagents for this colorimetric determination of LA were obtained from the Sigman Chemical Co., St. Louis, Mo. Solution A contained 1.6 mg/ml β-nicotinamide adenine dinucleotide and 0.03% (w/v) gelatin in a 0.6M glycine, 80 mM hydrazine buffer at pH 9.2. Solution B contained 166 units/ml lactate dehydrogenase, 0.5 mg/ml p-Iodonitrotetrazolium violet, and 0.03 mg/ml phenazine methosulfate in water. A LA standard solution diluted in phosphate buffered saline served as a positive control for the assay, and a solution of 0.35N HCl was used to stop the reaction. A 96-well microtiter plate (Dynatech) which contained 0.05 ml of solution A in each well was used as the reaction plate to determine the amount of LA in a 0.015 ml sample obtained from corresponding wells of the biological assay microtiter plates.

The addition of 0.05 ml of solution B to each well in the reaction plate started the reaction, and after sufficient time for reduction of the tetrazolium dye, the reaction was stopped by the addition of 0.05 ml of the HCl solution to each well. The optical density of 550 nm of each well of the reaction plate was then determined with a microplate spectrophotometer (Artek Model 200). A unit of IL-2 activity is defined as a quantity of IL-2 which produces a half-maximal response in the assay. The IL-2 concentration is calculated as the reciprocal of the dilution in the 50% endpoint well. National Institutes of Health Bureau of Biological Response Modifiers (BRMP) Reference Reagent Human IL-2 (Jurkat) material was used as a standard.

IL-2 receptor measurements were made using the double epitope ELISA method of Rubin et al., *J. Immunol.* 135:3172 (1985). Units of IL-2 receptor activity are as defined by Rubin et al., *J. Immunol.* 135:3172 (1985), which is hereby incorporated by reference.

6.2. PREPARATION OF INTERLEUKIN-2

Nonglycosylated mature recombinant human IL-2 was produced in transformed *E. coli* and glycoslyated recombinant human IL-2 was produced in transfected mammalian cells, using methods known in the art. See Taniguchi et al., *Nature* (London) 302:305 (1983); European patent application publication No. 0 091 539 A1 and U.S. patent application Ser. No. 463,496 now U.S. Pat. No. 4,738,927, which are hereby incorporated by reference. IL-2 from lysates of the bacterial cells and from culture medium conditioned by the mammalian cells was purified as described below.

In a preferred embodiment, recombinant IL-2 was produced in *E. coli* by isolating a cDNA clone coding for human IL-2 using synthetic oligonucleotides based on the DNA sequence of Taniguchi et al. ([Nature (London) 302:305 (1983); hereby incorporated by reference] and then using the clone to construct the expression plasmid pRC 233/IL-2/Δtet. This plasmid and the method for its construction are detailed in Ju et al., *J. Biol. Chem.* 262:5723 (1987), which is hereby incorporated by reference. Transformants containing the plasmid were cultured under standard conditions.

In another preferred embodiment, recombinant IL-2 was produced in a dihydrofolate reductase deficient Chinese Hamster Ovary cell line (CHO/dhFr−) transfected with the human UK-2 gene. The gene was incorporated into eukaryotic expression vector pBC12MI to produce vector pBC12/RSV/IL-2/dhFr by a series of steps, transfected into the CHO cells and expressed as described by Cullen in U.S. patent application Ser. No. 862,082, filed May 12, 1987 for "Enhanced Expression of Human Interleukin-2 In Mammalian Cells" now U.S. Pat. No. 4,992,367, which is hereby incorporated by reference. Vector pBC12MI contains the active Rous Sarcoma Virus long terminal repeat promoter and polyadenylation signals derived from the rat preproinsulin II gene.

6.3. PRODUCTION AND PURIFICATION OF RECOMBINANT SOLUBLE IL-2 RECEPTORS

A secreted form of the human IL-2 receptor was produced in mammalian cells using methods known in the art. See Treiger et al., J. Immunol. 136:4099 (1986), which is hereby incorporated by reference. Supernatant medium from the cultured cells containing the secreted IL-2 receptors (IL-2R) was collected for purification.

In a preferred embodiment, plasmid pIL2R3 described by Treiger et al., supra, was cleaved with the restriction enzyme Nae I to excise an 879 bp IL-2R gene fragment containing the entire 816 bp IL-2R coding sequence flanked by 24 bp of 5' and 39 bp of 3' noncoding sequences. The IL-2R cDNA was blunt-ended Hind III and Bam HI sites of the pBC12MI expression vector described above, using T4 DNA ligase. The expression vector subclone containing the desired IL-2R cDNA insert in the correct orientation was designated pBC12/IL-2R.

Vector pBC12/IL-2R Nae was obtained from pBC12/IL-2R by cleavage at the unique IL-2R gene Nae I site and at a unique vector Sma I site, and a 14 bp oligonucleotide containing termination codons in all three reading frames (5'-TTAAGTTAACTTAA-3') was inserted. Vector pBC12/IL-2R Nae encodes a truncated IL-2R gene lacking the carboxy terminal 28 amino acids (similar to the gene of Treiger et al., supra) and containing added codons for leucine and serine (5'-TTAAGT-3').

Plasmid pBC12/IL-2R Nae was used to transfect CHO/dhFr− cells by the method of Cullen, supra, as described above for recombinant IL-2 production, and recombinant IL-2R was produced in medium conditioned by cultures of such transfected cells.

The conditioned medium from the transfected CHO cells was concentrated ten-fold by diafiltration in a millipore Pellicon ® system using a PTGC cassette with 10,000 dalton retention. The concentrated supernatant (1,200 ml) was applied to an IL-2 affinity column (4.4×6.5 cm) containing nonglycosylated mature recombinant human IL-2 covalently coupled to Polyhydroxy NuGel-AF ® support (Separation Industries, Metuchen, N.J.) at a coupling density of 4.7 mg/ml gel. Polyhydrogen NuGel-AF ® is a modified polymeric silica having 3-[3-(2,3-dihydroxy)propoxy]propyl-groups of the formula

The IL-2 was coupled to the solid support material, after periodate oxidation of the support, by reductive amination in the presence of sodium cyanoborohydride as described by Roy et al., J. Chromatogr. 303:225 (1984).

Unadsorbed contaminating materials were removed by a phosphate buffered saline (PBS) wash, and the specifically adsorbed IL-2R was desorbed with 3M JSCN in PBS. After dialysis against PBS, the affinity column eluate was applied to a 4.4×20.5 cm DEAE-silica column (NuGel P-DE 200 ®, Separation Industries). The IL-2R was eluted from the column with 0.2M NaCl in PBS, and a strongly bound major contaminant eluted with a subsequent 1M NaCl elution step.

The purified IL-2R was found to be a mixture of monomer and a reducible dimer, as determined by SDS polyacrylamide gel electrophoretic analysis under reducing and non reducing conditions. These two forms of the IL-2R were separated from each other by gel filtration in Sephacryl ® S-200 (Pharmacia Fine Chemicals, Piscataway, N.J.) using PBS as the eluent. The monomeric form of the purified IL-2R had a specific activity of $3.5 \times 10^8$ units/mg protein.

6.4. IMMOBILIZATION OF IL-2 RECEPTORS

Purified monomeric IL-2R was immobilized on NuGel P-AF ® poly-N-hydroxysuccinimide (PNHS; 500 Å, 40–60 μm; Separation Industries, Metuchen, N.J.). NuGel P-AF ® poly-N-hydroxysuccinimide is a modified polymeric silica having 3-[2-[[[2-[2-[(2,5-dioxo-1-pyrrolidinyl)oxy]-2-oxoethyl]amino]ethoxy]propyl-groups of the formula The following procedure was used. Twenty grams of dry PNHS (equivalent to 28 ml of swollen gel) were transferred into a 150 ml coarse sintered glass funnel and washed quickly with three 28-ml volumes of cold water. The washed gel was quantitatively transferred to a stoppered 100 ml Erlenmeyer flask containing 28 ml of a 2.1 mg/ml solution of the IL-2R in 0.1M potassium phosphate with 0.1M NaCl, pH 7.0. The mixture was shaken gently at 4° C. for 16 hours, after which uncoupled IL-2R was collected by filtering the reaction mixture. The gel was washed with two 28-ml volumes of PBS, and the filtrate and washes were combined and dialyzed against 2 liters of PBS overnight at 4° C.

Immediately after washing, the gel was combined with 28 ml of 100 mM ethanolamine-HCl, pH 7.0, and shaken for one hour to neutralize any remaining unreacted NHS-ester groups. The IL-2R gel was washed three times with 28-ml volumes of PBS and then stored in the same buffer with 0.1% sodium azide at 4° C.

The dialysate volume was measured and the protein value was determined spectrophotometrically at 280 nm, based upon an optical density at that wavelength of 1.65 for a 1 mg/ml IL-2R solution. Calculations based on the difference between the starting amount of IL-2R used (58.8 mg) and the amount of uncoupled IL-2R recovered in the dialysate (29.4 mg) showed that the coupling density of the IL-2R was 1.05 mg protein/ml of swollen gel.

6.5. PURIFICATION OF RECOMBINANT IL-2 FROM E. COLI

A cell paste of E. coli transformed with a plasmid containing the human IL-2 gene was uniformly suspended in 30 mM Tris-HCl, pH 8.0, containing 5 mM ethylenediaminetetraacetic acid (EDTA) [Buffer A, 4 ml/g of cells] and stirred at 2°–8° C. The suspension was passed through a Gaulin homogenizer (APV Gaulin, Everett, Mass.) two or three times at 7,000 psi, with the homogenizer exit temperature maintained at 2°–8° C. with a dual heat transfer coil.

The cell lysate was centrifuged at 24,000 x g for one hour in a Sorvall RC-5B centrifuge with a GSA rotor (DuPont, Wilmington, Del.), and the supernatant fluid containing soluble proteins was discarded. The pellet was suspended in Buffer A (4 ml/g of cells) and stirred for 30 to 60 minutes at 4° C. After centrifugation as above, the supernatant fluid was discarded.

The pellet was suspended in 1.75M guanidine-HCl (4 ml/g) and mixed for 30 minutes to one hour as described before. The supernatant fluid was discarded, and the pellet was suspended in 7M guanidine-HCl (4 ml/g cells) and stirred for one hour. The extract was centrifuged as above, and the resulting supernatant fluid was diluted 40-fold with PBS and allowed to stand for 24 hours at 4° C. While the solution was standing, flocculent debris developed. The diluted supernatant fluid was carefully decanted from the settled flocculent debris and then concentrated 10-fold in a Millipore-Pellicon system.

An IL-2 receptor-affinity column was prepared by packing 19 ml (settled volume) of the immobilized IL-2R gel described above into an Amicon G-16×250 column fitted with two adapters. The column was equilibrated with PBS, after which 160 ml of the concentrated E. coli extract derived from 10 g of cells was applied to the column. The column was run at a flow rate of 4 ml/minute, and the effluent was monitored with a Gilson 111B UV detector connected to a Kippen Zonen recorder (Gilson Medical Electronics, Inc., Middletown, Wis.).

The column was washed with 5 bed volumes of PBS or until the effluent absorbance at 280 nm returned to baseline, after which the bound recombinant IL-2 was desorbed from the column using 1-2 bed volumes of 0.2N acetic acid containing 0.2M NaCl. The collected IL-2 fraction was concentrated in a stirred cell Amicon concentrator fitted with a YM 5 membrane.

The IL-2 -activity and the amount of protein from the various fractions of the purification procedure were determined, with the results shown in Table 1.

TABLE 1

Purification of Recombinant IL-2 From E. coli

| Fraction | Volume (ml) | Protein (mg) | Activity (Units × $10^{-6}$) | Activity Recovery (%) | Specific Activity (U/mg × $10^{-7}$) |
|---|---|---|---|---|---|
| Extract | 160 | 80.0 | 416 | 100 | 0.52 |
| Flow-through | 170 | 61.4 | 250 | 60 | 0.41 |
| Affinity Pool | 16 | 11.2 | 179 | 43 | 1.60 |

In Table 1, the initial extract was compared with material which did not bind to the column (flow-through) and with IL-2 which specifically bound to the column but was eluted with the acetic acid solution. The data of Table 1 show that only about 43% of the IL-2 activity in the guanidine-HCl extract of the insoluble fraction of the bacterial lysate specifically bound to the column, while the remainder of the applied activity passed directly through the column.

Analysis of the flowthrough by SDS polyacrylamide gel electrophoretic analysis (FIG. 5, lane 2) showed that the IL-2 contained therein was primarily in aggregated, higher molecular weight forms. By allowing the diluted extract described above to stand for several days instead of 24 hours, however, the percentage of monomeric IL-2 increased. When extracts thus treated were applied to the IL-2 receptor-affinity column, more than 90% of the total IL-2 activity specifically bound to the column.

6.6. PURIFICATION OF RECOMBINANT IL-2 FROM MAMMALIAN CELLS

Three liters of conditioned cell culture medium were applied to the IL-2 receptor-affinity column described above, and the mammalian recombinant IL-2 was purified as previously described for the E. coli recombinant IL-2.

The IL-2 activity and the amount of protein from the various fractions of the purification procedure were determined, as shown in Table 2.

TABLE 2

Purification of Recombinant IL-2 from Mammalian Cell Conditioned Medium

| Fraction | Volume (ml) | Protein (mg) | Activity (Units × $10^{-7}$) | Activity Recovery (%) | Specific Activity (U/mg × $10^{-7}$) |
|---|---|---|---|---|---|
| Starting Medium | 3,000 | 13,500 | 15.5 | 100 | n.d. |
| Flow-through | 3,000 | 13,500 | 0.5 | 3 | n.d. |
| Affinity Pool | 14 | 7.9 | 13.8 | 89 | 1.8 | n.d. means that the specific activity values for the starting medium and for the material not binding to the column were not determined. Such values would be meaningless due to the high levels of serum used in the cell cultures.

The data of Table 2 show that most of the IL-2 in the conditioned medium specifically bound to the affinity column, and the overall recovery of activity approached 90%. This higher percentage of binding and recovery compared to the bacterially produced recombinant IL-2 appears to be due to a much lower degree of aggregate formulation in the mammalian cell culture expression system.

6.7. ANALYSIS OF THE PURIFIED IL-2s

To determine the degree of aggregation of the recombinant IL-2's obtained from the affinity pools, the mammalian and bacterial cell products were subjected to gel filtration in superfine Sephadex ® G-50. A Pharmacia K 26/40 column was packed to a bed height of 35 cm, and the column was equilibrated with 50 mM sodium acetate, pH 3.5, containing 200 mM NaCl and 5 mg/ml mannitol (ICI Americas, Inc., Wilmington, Del.).

Volumes of the affinity pools (14-16 ml) were concentrated to 3 ml before application, and the columns were run at a flow rate of 0.5 ml/min using the equilibration buffer. Ten-minute fractions were collected on an LKB Ultra Rac-7000 fraction collector (LKB-Produkter, Brommer, Sweden), and the effluent was monitored at 280 nm with a Gilson Model 111B UV detector connected to a Kippen Zonen recorder. The results are shown in FIGS. 2 (recombinant IL-2 from E. coli) and 3 (recombinant IL-2 from mammalian cells).

Figure 2:
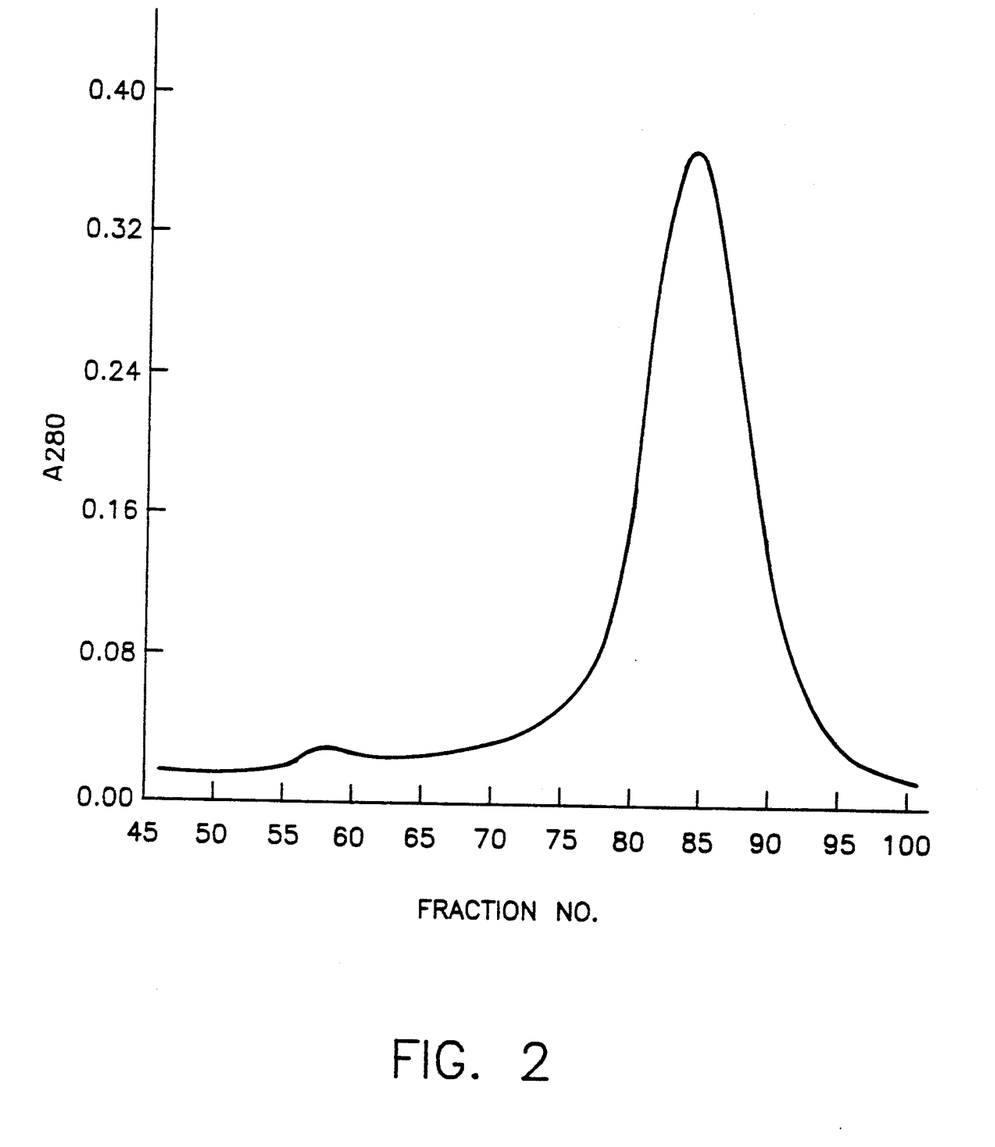
FIG. 2 is a Sephadex ® G-50 column elution profile of recombinant human IL-2 produced in *E. coli* and purified by receptor-affinity chromatography.
Figure 3:
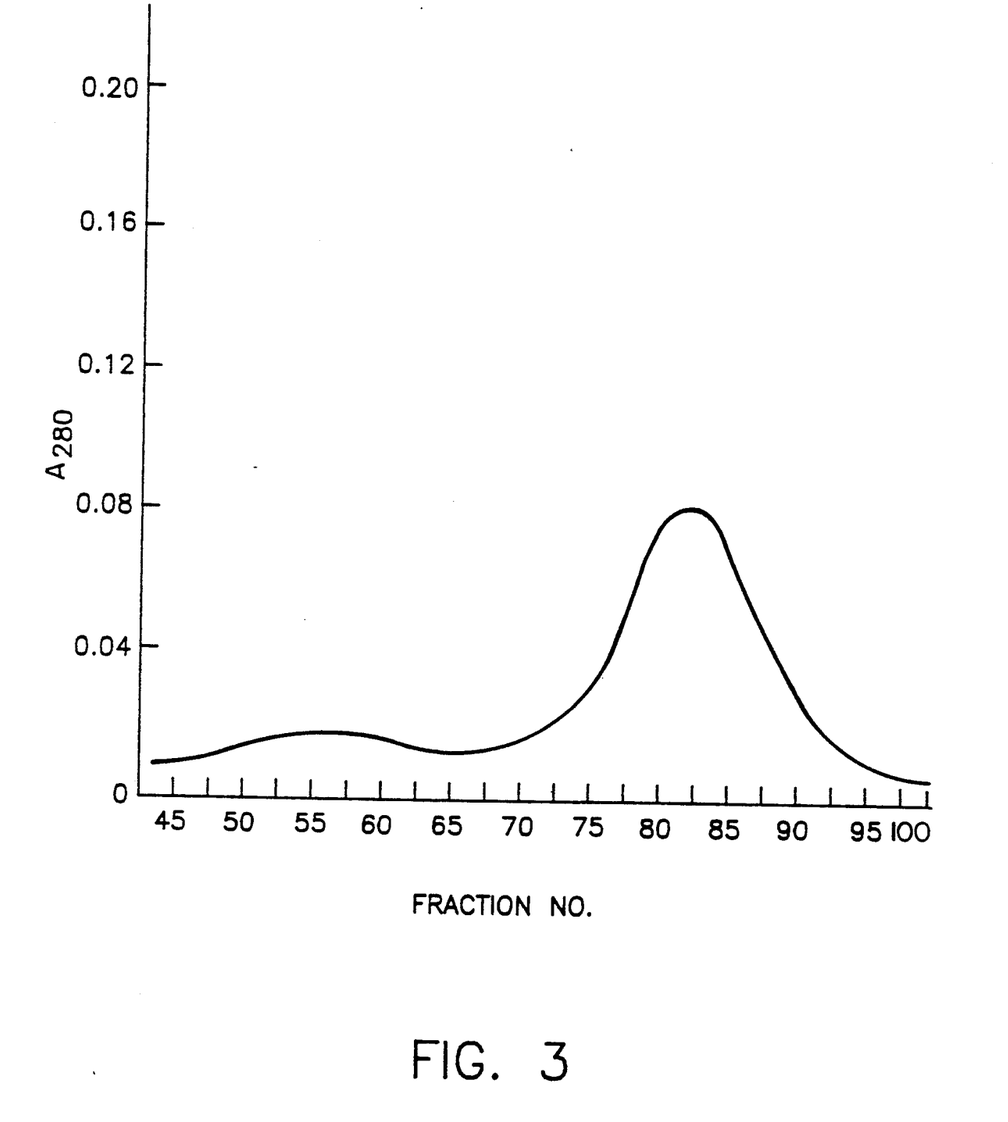
FIG. 3 is a Sephadex ® G-50 column elution profile of recombinant IL-2 produced in mammalian cells and purified by receptor-affinity chromatography.

FIGS. 2 and 3 show that most of the recombinant IL-2s eluted in a peak centered at about fraction 83. This material ran at a position in the elution profiles expected for monomeric IL-2. In both figures only a very small amount of higher molecular weight material was seen (peaking at about fraction 57). Thus, recombinant human IL-2, whether produced in a bacterial or a mammalian cell expression system, emerges from the IL-2 receptor-affinity column in an essentially unaggregated, monomeric form. In marked contrast, bacterially produced recombinant IL-2 purified on an immunoaffinity column contains a high degree of aggregated material.

A murine monoclonal antibody designated 5B1 and directed against a dodecapeptide having an amino acid sequence corresponding to the N-terminal twelve amino acid residues of human IL-2 was prepared as described by Chizzonite in U.S. patent application Ser. No. 840,229, filed Mar. 17, 1986 for "Monoclonal Antibodies To Interleukin-2" now abandoned which is hereby incorporated by reference. Monoclonal antibody 5B1 was purified from BALB/c mouse ascites fluid using ammonium sulfate precipitation followed by anion exhange chromatography, as described by Staehelin et al., J. Biol. Chem. 256:9750 (1981).

The purified antibody was immobilized on Nugel P-AF ® poly-N-hydroxysuccinimide at an antibody loading of 11.8 mg/ml gel, as described above for the coupling of IL-2R. A 3.2×13 cm column packed with this immunoaffinity adsorbent was used to purify recombinant human IL-2 expressed in $E.\ coli$, using the same protocol described above for the purification of IL-2 in the receptor-affinity column.

Figure 4:
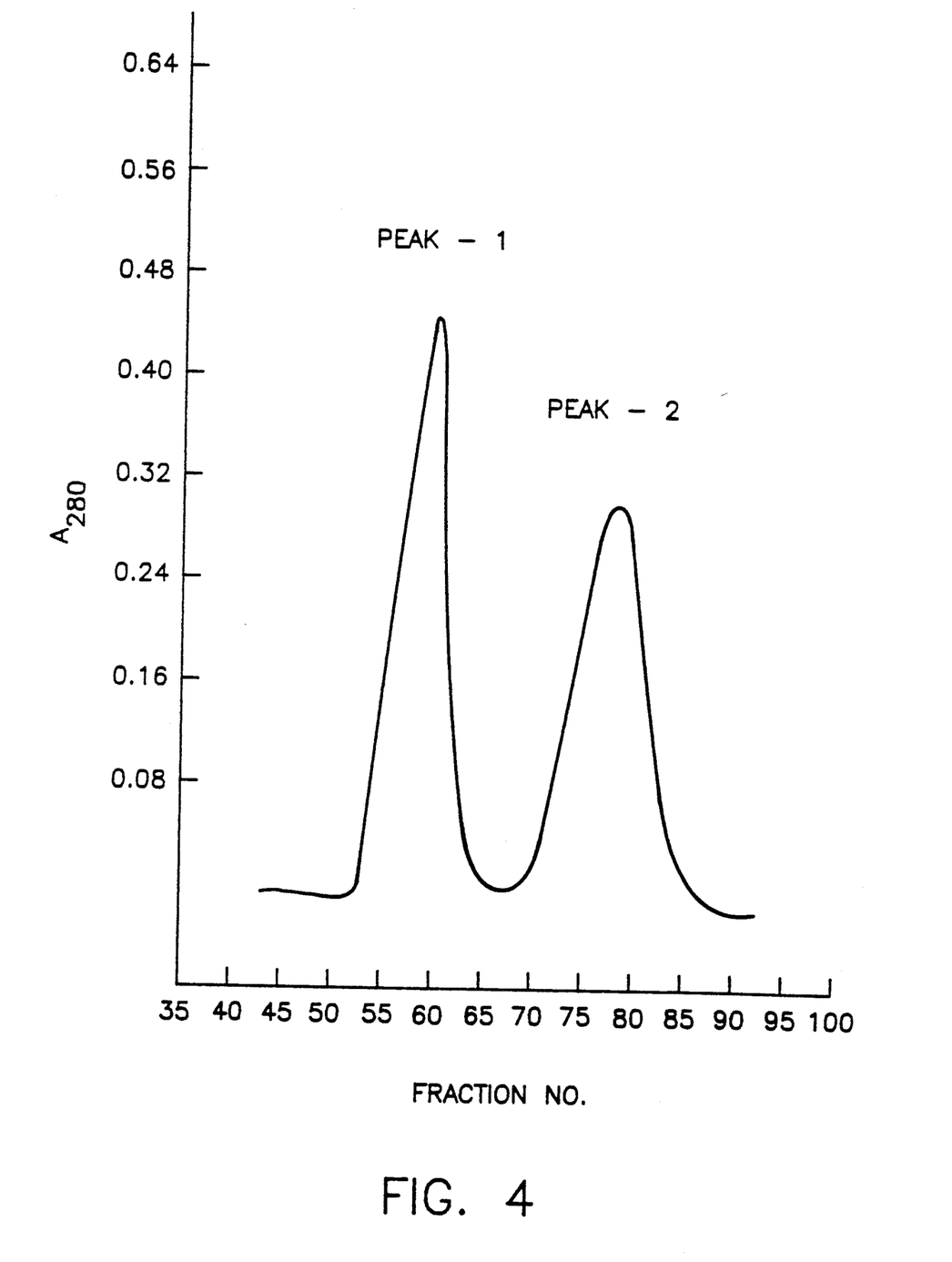
FIG. 4 is a Sephadex ® G-50 column elution profile of recombinant human IL-2 produced in *E. coli* and purified by immunoaffinity chromatography.

Recombinant IL-2 purified in this column was subjected to gel filtration in Sephadex ® G-50 as described above, with the results shown in FIG. 4. This figure shows that a large amount of the immunoaffinity purified IL-2 (identified as peak 1) was in a higher molecular weight, or aggregated oligomeric form. Unaggregated, monomeric IL-2 is in peak 2.

To confirm that the material specifically bound and later eluted from the IL-2 receptor-affinity column was in fact IL-2, samples from the affinity pools were subjected to amino acid composition analysis, with the results shown in Table 3.

TABLE 3

Amino Acid Compositions of Purified Recombinant IL-2s

| Amino Acid | Residues In IL-2 From | | |
|---|---|---|---|
| | E. Coli* | Mammalian Cells | Expected |
| Aspartic acid | 12.6 | 11.7 | 12 |
| Threonine | 12.5 | 12.3 | 13 |
| Serine | 7.2 | 7.3 | 8 |
| Glutamic Acid | 18.5 | 17.2 | 18 |
| Proline | 5.1 | 3.9 | 5 |
| Glycine | 2.3 | 3.0 | 2 |
| Alanine | 5.5 | 4.7 | 5 |
| Cysteine | 3.0 | 3.4 | 3 |
| Valine | 4.0 | 3.7 | 4 |
| Methionine | 4.5 | 3.9 | 4 |
| Isoleucine | 8.0 | 8.1 | 9 |
| Leucine | 22.1 | 23.4 | 22 |
| Tyrosine | 3.0 | 3.7 | 3 |
| Phenylalanine | 6.9 | 6.5 | 6 |
| Histidine | 3.1 | 3.1 | 3 |
| Lysine | 10.3 | 11.3 | 11 |
| Arginine | 4.0 | 4.2 | 4 |
| Tryptophan | 0.9 | 1.3 | 1 |
| Total | 133 | 133 | 133 |

*Average of two analyses

As shown in Table 3, the amino acid compositions of both of the purified recombinant IL-2s were in close agreement with the expected values for IL-2.

Figure 5:
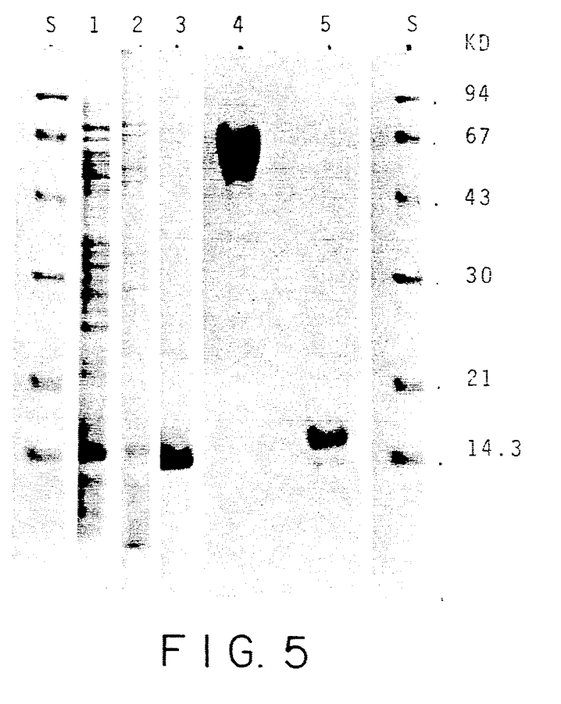
FIG. 5 shows the results of an SDS-polyacrylamide gel electrophoretic analysis under nonreducing conditions of a mixture of standard molecular weight marker proteins (lanes S); a recombinant *E. coli* extract (lane 1); flowthrough from the purification of the *E. coli* extract in the receptor-affinity column (lane 2); receptor-affinity purified recombinant IL-2 from the *E. coli* extract (lane 3); conditioned medium from transfected mammalian cells producing recombinant IL-2 (lane 4); and receptor-affinity purified recombinant IL-2 from the conditioned medium (lane 5). Numbers to the right of the gels are the molecular weights of the marker proteins in kilodaltons.

An assessment of the purity of the receptor-affinity purified recombinant IL-2s was made by SDS-polyacrylamide gel electrophoretic analysis as shown in FIG. 5. The analysis was carried out under nonreducing conditions (i.e., without mercaptoethanol).

In FIG. 5, lanes S contained a mixture of molecular weight marker proteins including phosphorylase B (94 Kd), bovine serum albumin (67 Kd), ovalbumin (43 Kd), carbonic anhydrase (30 Kd), soybean trypsin inhibitor (21 Kd) and lysozyme (14.3 Kd). Lanes 1–5 contained 20 μg protein amounts of whole extract from the recombinant $E.\ coli$ producing IL-2; flowthrough from the purification of the $E.\ coli$ extract in the receptor-affinity column; receptor-affinity purified recombinant IL-2 from the $E.\ coli$ extract; conditioned medium from the transfected mammalian cells producing recombinant IL-2 from the conditioned medium, respectively. The molecular weights of the marker proteins in kilodaltons are shown to the right of the gels. The gels were stained with Coomassie blue to visualize the protein bands.

FIG. 5 shows that by use of the single receptor-affinity step, the recombinant IL-2 in the crude bacterial extract was purified to produce a major band and a more slowly migrating minor band (lane 3). The figure also shows that by the use of the same single affinity purification step, the recombinant IL-2 in the mammalian cell conditioned medium was purified to produce a major band and a minor, more rapidly migrating band (lane 5). Analysis by Western blotting showed that all of the bands observed in lanes 3 and 5 contained IL-2.

The Western blotting analysis was carried out as described by Burnett [Anal. Biochem. 112:195 (1981)] and by Towbin et al. [Proc. Natl. Acad. Sci. U.S.A. 76:4350 (1979)]. The antibodies used were monoclonal antibodies 13A6 and 17A1 (specific for both glycosylated and nonglycosylated IL-2) and 5B1 (specific for nonglyosylated IL-2 only), which are described in Chizzonite, supra, and in Chizzonite et al., J. Biol. Chem. (In press) (1987).

6.8. RECEPTOR AFFINITY PURIFICATION OF IL-2 ANALOGS

Plasmids encoding analogs of recombinant human IL-2 were prepared using site-specific mutagenesis and recombinant DNA methodolgy and expressed in $E.\ coli$ as described by Ju et al., J. Biol. Chem. 262:5723 (1987). In one of these analogs, the amino-terminal alanine was deleted and the natural cysteine residue at position 125 was replaced by serine (des-Ala$^1$-Ser$^{125}$ IL-2). In another analog, the natural aspartic acid residue at position 20 was replaced by lysine (Lys$^{20}$ IL-2). The specific biological activities of the recombinant des-Ala$^1$-Ser$^{125}$ and Lys$^{20}$ IL-2s were $1.7 \times 10^7$ and $2.2 \times 10^4$ U/mg protein, respectively, after purification as shown below.

Figure 6:
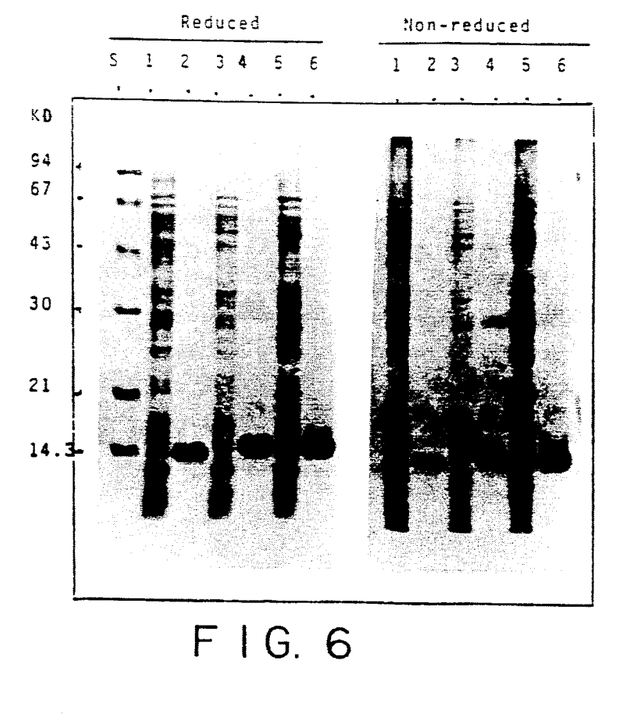
FIG. 6 shows the results of an SDS-polyacrylamide gel electrophoretic analysis under both reducing and non-reducing conditions of a mixture of standard molecular weight marker proteins (lane S), *E. coli* extract containing des-Ala$^1$-Ser$^{125}$ IL-2 (lanes 1), affinity purified des-Ala$^1$-Ser$^{125}$ IL-2 (lanes 2), *E. coli* extract containing Lys$^{20}$IL-2 (lanes 3), affinity purified Lys$^{20}$IL-2 (lanes 4), *E. coli* extract containing wild type recombinant human IL-2 (lanes 5), and affinity purified wild type recombinant human IL-2 (lanes 6). The numbers to the left of the figure are the molecular weights of the marker proteins.

The des-Ala$^1$-Ser$^{125}$ IL-2 and the Lys$^{20}$ IL-2 were purified in the IL-2 receptor-affinity column as described above, and the affinity pools were analyzed by SDS polyacrylamide gel electrophoresis as before. The results are shown in FIG. 6, in which the lanes contain a mixture of molecular weight marker proteins (lane S), $E.\ coli$ extract containing des-Ala$^1$-Ser$^{125}$ IL-2 (lanes 1), affinity purified des-Ala$^1$-Ser$^{125}$ IL-2 (lanes 2), $E.\ coli$ extract containing Lys$^{20}$ IL-2 (lanes 3), affinity purified Lys$^{20}$ IL-2 (lanes 4), $E.\ coli$ extract containing wild type recombinant human IL-2 (lanes 5), and affinity purified wild type recombinant human IL-2 (lanes 6). The IL-2 containing samples were run under both reducing and nonreducing conditions as indicated (with and without reduction by mercaptoethanol). The numbers to the left of the figure are the molecular weights of the marker proteins.

FIG. 6 shows that the IL-2 receptor-affinity adsorbent of this invention can be used to purify variants of IL-2 having amino acid deletions and/or substitutions and intrinsic specific biological activities differing by several orders of magnitude, as well as the wild type recombinant IL-2. For all of these IL-2s, the affinity purified product is in an essentially unaggregated, monomeric and highly active form.

Many modifications and variations of this invention may be made without departing from its spirit and scope, as will be apparent to those skilled in the art. The specific embodiments described herein are offered by way of example only, and the invention is limited only by the terms of the appended claims.

What is claimed is:

1. An IL-2 cell surface receptor-affinity adsorbent comprising a solubilized TAC antigenic IL-2 cell surface receptor protein covalently bound to a solid support, which bound receptor molecules are capable of specifically binding substantially only the unaggregated, monomeric form of IL-2.

2. A method for purifying IL-2 in a solution or culture medium conditioned by human or animal cells producing IL-2, comprising:
   (a) contacting a solution or condition medium containing IL-2 with a receptor-affinity adsorbent comprising a solubilized TAC antigenic IL-2 cell surface reporter protein covalently bound to an insoluble support, which bound receptor molecules are capable of specifically binding substantially only the unaggregated, monomeric form of IL-2;
   (b) allowing the unaggregated, monomeric IL-2 to specifically bind to the adsorbent;
   (c) washing the adsorbent to remove unbound contaminating substances;
   (d) desorbing the IL-2 from the washed adsorbent; and
   (e) separating the receptor-affinity adsorbent from the desorbed IL-2.

3. A method for purifying recombinant IL-2 produced in a bacterial expression system, comprising:
   (a) disrupting cultured bacterial cells transformed by a vector capable of directing the expression of IL-2, to produce a cell lysate;
   (b) isolating the insoluble fraction from the cell lysate;
   (c) extracting the isolated insoluble fraction from the cell lysate with a solution of from about 4 to 7M guanidine-HCl to obtain an IL-2 containing extract;
   (d) diluting the IL-2 containing extract from about 10- to about 1,000-fold with a guanidine-HCl free solution;
   (e) contacting the diluted IL-2 containing extract with a receptor-affinity adsorbent comprising a solubilized TAC antigenic IL-2 cell surface receptor protein covalently bound to an insoluble support, which bound receptor molecules are capable of specifically binding substantially only the unaggregated monomeric form of IL-2;
   (f) allowing the IL-2 to specifically bind to the adsorbent;
   (g) washing the adsorbent to remove unbound contaminating substances;
   (h) desorbing the IL-2 from the washed adsorbent; and
   (i) separating the receptor-affinity adsorbent from the desorbed unaggregated, monomeric IL-2.

4. The method of claim 3 in which the extract of step (c) is diluted from about 30- to about 50-fold.

5. The method of claim 3 in which extraction step (c) is preceded by preextraction steps to extract contaminating cellular materials, comprising extracting the isolated insoluble fraction from the cell lysate with
   (i) a buffered salt solution; and
   (ii) a solution of from about 1.75 to 2M guanidine-HCl.

6. The method of claim 4 in which extraction step (c) is preceded by preextraction steps of extract contaminating cellular materials, comprising extracting the isolated insoluble fraction from the cell lysate with
   (i) a buffered salt solution; and
   (ii) a solution of about 1.75 to 2M guanidine HCl.

7. The method of claim 3 in which dilution step (d) is followed by a step comprising allowing the diluted extract to stand for a period of time ranging from about four hours to more than three days.

8. The method of claim 7 in which the diluted extract of step (d) is allowed to stand for about one to about three days.

9. The method of claim 4 in which dilution step (d) is followed by a step comprising allowing the diluted extract to stand for a period of time ranging from about four hours to more than three days.

10. The method of claim 9 in which the diluted extract of step (d) is allowed to stand for about one to about three days.

11. The method of claim 5 in which dilution step (d) is followed by a step comprising allowing the diluted extract to stand for a period of time ranging from about four hours to more than three days.

12. The method of claim 11 in which the diluted extract of step (d) is allowed to stand for about one to about three days.

13. The method of claim 6 in which dilution step (d) is followed by a step comprising allowing the diluted extract to stand for a period of time ranging from about four hours to more than three days.

14. The method of claim 13 in which the diluted extract of step (d) is allowed to stand for about one to about three days.

* * * * *

UNITED STATES PATENT AND TRADEMARK OFFICE
CERTIFICATE OF CORRECTION

PATENT NO. : 5,162,503
DATED : November 10, 1992
INVENTOR(S) : BAILON ET AL.

It is certified that error appears in the above-identified patent and that said Letters Patent is hereby corrected as shown below:

Column 2, line 30, delete "b" and insert therefore -- by --

Column 5, line 37, delete "molecular" and insert therefore -- molecule --

Column 5, line 45, insert therefore after the word "organic" -- , --

Column 7, line 7, after the word used. Delete "in" and insert therefore -- In --

Column 8, line 2, delete "Sigman" and insert therefore -- Sigma --

Column 9, line 65, delete "JSCN" and insert therefore -- KSCN --

Signed and Sealed this

Thirteenth Day of September, 1994

Attest:

BRUCE LEHMAN

Attesting Officer                Commissioner of Patents and Trademarks